(12) United States Patent
Wang et al.

(10) Patent No.: US 8,754,370 B1
(45) Date of Patent: Jun. 17, 2014

(54) SHEATHLESS INTERFACE FOR COUPLING CAPILLARY ELECTROPHORESIS WITH MASS SPECTROMETRY

(71) Applicants: Chenchen Wang, Richland, WA (US); Keqi Tang, Richland, WA (US); Richard D. Smith, Richland, WA (US)

(72) Inventors: Chenchen Wang, Richland, WA (US); Keqi Tang, Richland, WA (US); Richard D. Smith, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 0 days.

(21) Appl. No.: 13/788,854

(22) Filed: Mar. 7, 2013

(51) Int. Cl.
  *H01J 49/26* (2006.01)
  *H01J 49/16* (2006.01)
  *H01J 49/04* (2006.01)
  *G01N 30/72* (2006.01)

(52) U.S. Cl.
  CPC .......... *H01J 49/167* (2013.01); *H01J 49/0404* (2013.01); *H01J 49/0431* (2013.01); *G01N 30/7233* (2013.01)
  USPC ............................ 250/288; 250/281; 250/282

(58) Field of Classification Search
  CPC ... H01J 49/004; H01J 49/0404; H01J 49/167; H01J 49/0431; H01J 49/165; G01N 30/7233
  USPC ......................................... 250/281, 282, 288
  See application file for complete search history.

(56) References Cited

U.S. PATENT DOCUMENTS

| 5,993,633 | A | 11/1999 | Smith et al. | |
| 2006/0057556 | A1* | 3/2006 | Janini et al. | 435/4 |

| 2007/0267293 | A1 | 11/2007 | Finch et al. | |
| 2012/0318672 | A1 | 12/2012 | Sun et al. | |
| 2013/0327936 | A1* | 12/2013 | Ramsey et al. | 250/282 |

FOREIGN PATENT DOCUMENTS

WO   2005/096720 A2   10/2005

OTHER PUBLICATIONS

Moini, "Simplifying CE-MS Operation. 2. Interfacing Low-Flow Separation Techniques to Mass spectrometry Using a Porous Tip", Analytical Chemistry 2007, 79, pp. 4241-4246.*
International Search Report/Written Opinion for International Application No. PCT/US2013/064901l, International Filing Date Oct. 9, 2013.
Jussila, M., et al., Modified liquid junction interface for nonaqueous capillary electrophoresis-mass spectrometry, Electrophoresis. 2000, 21, 3311-3317.
Moini, M., et al., Simplifying CE-MS Operation. 2. Interfacing Low-Flow Separation Techniques to Mass Spectgrometry Using a Porous Tip, Anal. Chem., 79, 2007, 4241-4246.
Whitt, J. T., et al., Capillary Electrophoresis to Mass Spectrometry Interface Using a Porous Junction, Anal. Chem., 2003, 75, 2188-2191.
Bonvin, G., et al., Capillary electrophoresis-electrospray ionization-mass spectrometry interfaces: Fundamental concepts and technical developments, Journal of Chromatography A, 1267, 2012, 17-31.

(Continued)

*Primary Examiner* — Nicole Ippolito
(74) *Attorney, Agent, or Firm* — A. J. Gokcek

(57) ABSTRACT

A sheathless interface for coupling capillary electrophoresis (CE) with mass spectrometry is disclosed. The sheathless interface includes a separation capillary for performing CE separation and an emitter capillary for electrospray ionization. A portion of the emitter capillary is porous or, alternatively, is coated to form an electrically conductive surface. A section of the emitter capillary is disposed within the separation capillary, forming a joint. A metal tube, containing a conductive liquid, encloses the joint.

22 Claims, 5 Drawing Sheets

(56) References Cited

OTHER PUBLICATIONS

Wang, C., et al., Capillary Isotachophoresis—Nanoelectrospray Ionization—Selected Reaction Monitoring MS via a Novel Sheathless Interface for High Sensitivity Sample Quantification, Anal. Chem., 85, 2013, 7308-7315.

An, Y., et al., Selective enrichment and ultrasensitive identification of trace peptides in proteome analysis using transient capillary isotachophoresis/zone electrophoresis coupled with nano-ESI-MS, Electrophoresis, 27, 2006, 3599-3608.

Fang, X., et al., Application of capillary isotachophoresis-based multidimensional separations coupled with electrospray ionization-tandem mass spectrometry for characterization of mouse bran mitochondrial proteome, Electrophoresis, 29, 2008, 2215-2223.

Stegehuis, D. S., et al., Isotachophoresis as an on-line concentration pretreatment technique in capillary electrophoresis, Journal of Chromatography, 538, 1991, 393-492.

Wang, C., et al., Ultrasensitive Sample Quantitation via Selected Reaction Monitoring Using CITP/CZE-ESI-Triple Quadrupole MS, Analytical Chemistry, 84, 2012, 10395-10403.

Severs, J. C., et al., Characterization of the Microdialysis Junction Interface for Capillary Electrophoresis/Microelectrospray Ionization Mass Spectrometry, Analytical Chemistry, 69, 1997, 2154-2158.

\* cited by examiner

SHEATHLESS INTERFACE FOR COUPLING CAPILLARY ELECTROPHORESIS WITH MASS SPECTROMETRY

STATEMENT REGARDING FEDERALLY SPONSORED RESEARCH OR DEVELOPMENT

The invention was made with Government support under Contract DE-AC05-76RLO1830, awarded by the U.S. Department of Energy. The Government has certain rights in the invention.

TECHNICAL FIELD

This invention relates to separation and analysis of chemical and biological samples. More specifically, this invention relates to a sheathless interface that effectively couples capillary electrophoresis with electrospray ionization mass spectrometry, allowing high sample loading capacity, minimum sample dilution, and high sensitivity sample analysis.

BACKGROUND OF THE INVENTION

Capillary electrophoresis (CE) coupled with mass spectrometry (MS) has been well recognized as a complementary analytical technology to more conventional liquid chromatography-mass spectrometry (LC-MS). By combining the high resolving power of CE with the highly sensitive and information-rich detection of MS, this hyphenated technique has enjoyed successful applications in many fields of scientific research, such as biomarker discovery and verification, metabolomics, identification and quantification of environmental pollutants, and food quality control. Although much less widely applied than LC-MS, the number of publications related to development and application of CE-MS continues to increase because of its potential capability in performing sensitive and high-throughput sample analysis.

The major limitation to the broad applications of CE separation technique is its very limited sample loading capacity as compared to LC-based separation techniques. To overcome this limitation, alternative CE operation modes, such as a combination of capillary isotachophoresis (CITP) and capillary zone electrophoresis (CZE), also called transient isotachophoresis (tITP), were developed to increase the sample loading volume. A typical CITP/CZE separation can be performed efficiently with initial sample loading volume equal to ⅓ of the total separation capillary volume in the range of μL as compared to nL sample loading in traditional capillary zone electrophoresis (CZE) separation. In addition, CITP/CZE separation concentrates or focuses low abundance analytes to a much greater extent than the major components in a mixture, providing a selective enrichment of trace analytes. These two unique features of CITP/CZE—large sample loading volume and analyte focusing—have been explored extensively. CITP/CZE coupled with high sensitivity electrospray ionization mass spectrometry (ESI-MS) was recently shown to significantly improve the limit of detection in quantifying targeted peptides in complex biomatrix. It is highly possible that CITP/CZE-MS can outperform the conventional LC-MS in both sensitivity and separation efficiency if the operation of CITP/CZE-MS can be fully optimized, allowing the CITP/CZE sample loading volume to be comparable to that of LC.

What is needed is a robust interface that effectively couples CE with ESI-MS to allow large sample loading volume and stable ESI for highly sensitive CE-MS analysis.

SUMMARY OF THE INVENTION

A sheathless interface for coupling capillary electrophoresis (CE) with mass spectrometry is disclosed, in accordance with one embodiment of the present invention. The sheathless interface includes a separation capillary for performing CE separation and an emitter capillary for electrospray ionization. A portion of the emitter capillary is porous or, alternatively, is coated to form an electrically conductive or metallized surface. A section of the emitter capillary is disposed within the separation capillary, forming a joint. A metal tube, which contains an electrically conductive liquid, encloses the joint.

The outer diameter of the emitter capillary is smaller than an inner diameter of the separation capillary. In one embodiment, the inner diameter of the separation capillary is about 100 μm and the outer diameter of the emitter capillary is about 90 μm.

An emitter voltage is applied to the metal tube containing the electrically conductive liquid and a separation voltage is applied to a non-sealed end of the separation capillary. In one embodiment, the emitter capillary is sealed at the joint of the separation and emitter capillaries. In one embodiment, the non-sealed end of the emitter capillary is coupled to a mass spectrometer instrument. A liquid is pumped to the non-sealed end of the separation capillary.

The mass spectrometer instrument may be, but is not limited to, at least one of the following: a quadrupole mass spectrometer, a time of flight mass spectrometer, an ion trap mass spectrometer, Fourier transform ion cyclotron resonance mass spectrometer, and an orbitrap mass spectrometer.

The CE separation includes, but is not limited to, at least one of the following: capillary zone electrophoresis (CZE) separation, capillary isotachophoresis (CITP), capillary Isoelectric Focusing (CIEF), and capillary electrochromatography.

In another embodiment of the present invention, a method of providing a sheathless interface for coupling capillary electrophoresis with mass spectrometer is disclosed. The method includes disposing a section of an emitter capillary within a separation capillary, thereby forming a joint. The method also includes chemically etching a portion of the emitter capillary to form a porous capillary wall. The method further includes enclosing the joint in a metal tube that contains conductive liquid for electric contact. In another embodiment of the present invention, a method of providing a sheathless interface for coupling capillary electrophoresis with mass spectrometry is disclosed. The method includes disposing a section of an emitter capillary within a separation capillary, thereby forming a joint. The method also includes coating a portion of the emitter capillary to form a metallized surface. The method further includes enclosing the joint in a metal tube that contains conductive liquid for electric contact.

DETAILED DESCRIPTION OF THE PREFERRED EMBODIMENTS

The present invention is directed to a sheathless interface that effectively couples capillary electrophoresis (CE) with electrospray ionization (ESI) mass spectrometry (MS), allowing high sample loading capacity, minimum sample dilution, ad high efficiency ESI or nano-ESI operation. As used herein, a sheathless CE-MS interface is an interface without the use of a co-flow of sheath liquid to make an electric contract with the CE separation liquid at the tip of an ESI emitter. The sheathless interface design described herein involves, in one embodiment, the use of two capillaries with different inner diameters. The capillary with the larger inner diameter is used as a capillary isotachophoresis (CITP)/capillary zone electrophoresis (CZE) separation capillary for achieving large sample loading volume. The capillary with the smaller inner diameter is used as an ESI emitter capillary for ESI (or nanoESI) operation. In one embodiment, a separation voltage is applied to the separation capillary and an ESI voltage is applied to the ESI capillary. Conductivity is maintained through the entire device or interface using a conductive liquid.

The interface design of the present invention optimizes the performance of CITP/CZE-MS, enabling it to outperform conventional LC-MS and reach a performance level comparable to the high performance capillary LC-MS in both sensitivity and separation efficiency. Use of the sheathless interface of the present invention extends the limit of quantitation to 10 pM with 25 attomoles total sample loading. The present invention can be widely applied for ultrasensitive and fast analysis in academic research, pharmaceutical analysis, clinical analysis, and other fields of application.

Figure 1:
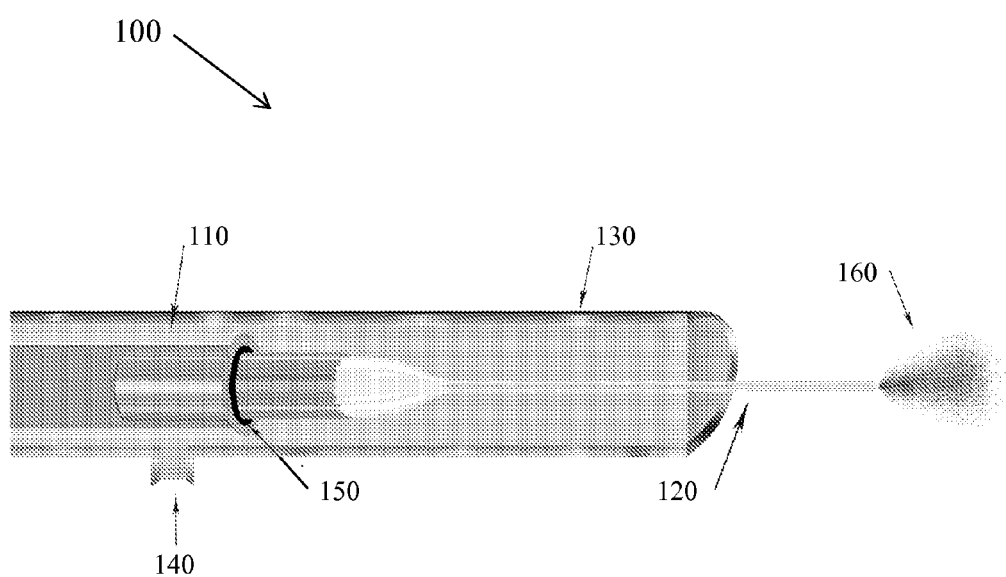
FIG. 1 illustrates a sheathless interface for coupling CE with MS, in accordance with one embodiment of the present invention.

FIG. 1 illustrates a sheathless interface 100 for coupling CE with MS, in accordance with one embodiment of the present invention. The sheathless interface 100 includes a separation capillary 110 for performing CE separation, an emitter capillary 120 for electrospray ionization 160, and a metal tube 130 containing a conductive liquid 140. A section of the emitter capillary 120 is disposed within the separation capillary 110. The selection of the capillaries 110 and 120 is such that an outer diameter of the ESI emitter capillary 120 is smaller than the inner diameter of the separation capillary 110 so that the emitter capillary 120 can slide into the separation capillary 110 and be sealed at a joint 150 of the separation and emitter capillaries 110 and 120.

In one embodiment, a portion of the emitter capillary wall can be further chemically etched to porous to form a sheathless CITP/CZE-ESI interface. The joint 150 can then be enclosed in the metal tube 130 filled with the conductive liquid 140 for electric contact. The term "enclosed" or "enclosing" should interpreted broadly to also include "partially enclosed" or "partially enclosing". As an example, the tube 130 may enclose all of the joint 150 or at least a portion of it. A high voltage can be applied to the metal tube 130 for ESI 160 or nanoESI operation while a separation voltage can be applied to the free end of the separation capillary 110. By using the combination of large inner diameter separation capillary 110 and small outer diameter emitter capillary 120, the interface 100 has shown to allow both larger sample loading capacity and stable ESI operation in a wide flow rate range (low nL/min to µL/min). This detachable sheathless interface 100 also provides the needed flexibility to accommodate different experimental operating conditions as different inner diameter ESI emitter capillaries that can be connected to a given separation capillary of different diameter lengths, and the ESI emitter capillary can be replaced readily without the need to replace the specially treated separation capillary.

This interface 100 can be further implemented with different setups involving the use of different CE separation modes and a different emitter capillary, such as a metal coated emitter capillary to form a conductive or metallized surface, to achieve higher analysis sensitivity. Also, the metal tube 130 can be any conductive tube.

Figure 2:
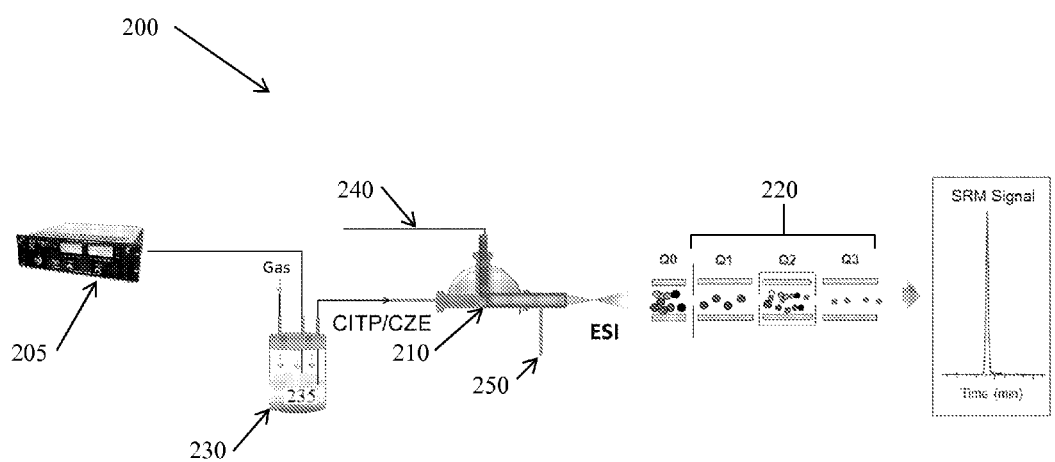
FIG. 2 illustrates the coupling of CITP/CZE with a triple quadrupole mass spectrometer using the sheathless interface shown in FIG. 1, in accordance with one embodiment of the present invention.

FIG. 2 illustrates the coupling 200 of CITP/CZE with a triple quadrupole mass spectrometer 220—operating in selected reaction monitoring (SRM) mode for sample quantitation—using the sheathless interface 100 shown in FIG. 1 in accordance with one embodiment of the present invention. In this embodiment the large CITP/CZE separation capillary (for example, 360 µm outer diameter, 100 µm inner diameter, and 95 cm long) was joint with a smaller ESI emitter capillary (for example 90 µm outer diameter, 20 µm inner diameter, and 4 cm long). A section of the emitter capillary, approximately 3 cm long, at the open end of emitter capillary was chemically etched using HF to porous, and the joint 210 was subsequently sealed using Epoxy. The joint 210 was then enclosed in a short metal tube filled with conductive liquid 240 for electric contact. Liquid samples of reservoir 235 in jar 230 were pumped to the separation capillary at a constant pressure. A high voltage 250 was applied to the metal tube for nanoESI operation while a CITP/CZE separation voltage 205 was applied to the free end of the large separation capillary.

Still referring to FIG. 2, ion guide Q0 interacts with the ESI source prior to the triple quadrupole MS 220. Specific mass-to-charge (m/z) precursor ions were selected in the first quadrupole Q1 and fragmented in the second quadrupole Q2 via collision-induced dissociation under sufficient collision energy. The specific m/z product ions were then selected in the third quadrupole Q3 and monitored by the MS detector. Through monitoring the unique transitions of the selected analytes, both high sensitivity and specificity can be achieved in sample quantification.

Figure 3:
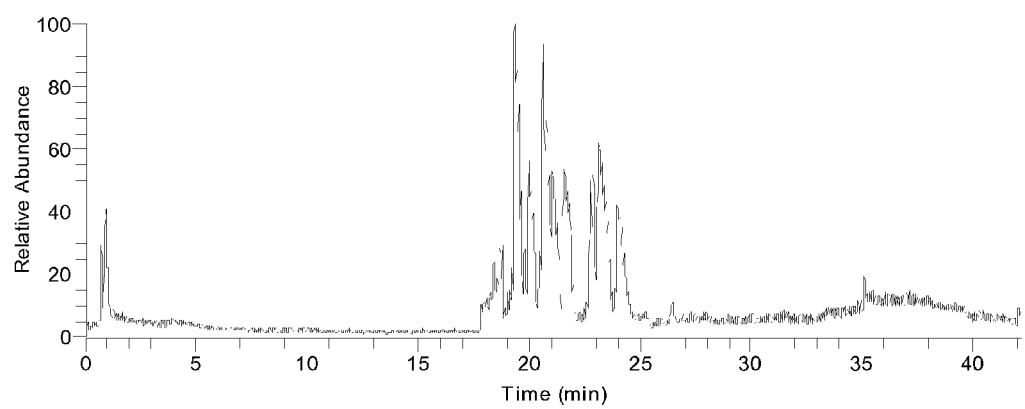
FIG. 3 shows the total ion chromatogram of CITP/CZE-MS analysis using a mixture of ten peptides.

The performance of CITP/CZE-MS shown in FIG. 2 was initially evaluated experimentally using a mixture of ten peptides, including bradykinin, angiotensin I, neurotensin, fibrinopeptide, substance P, kemptide, leu-enkephalin, angiotensin II, melittin, and renin, at concentration of 3.75 µM each in 25 mM ammonium acetate. The CITP/CZE separation voltage and nanoESI operating voltage used in the experiment were 30 kV and 1.6 kV, respectively. FIG. 3 shows the total ion chromatogram of the CITP/CZE-MS analysis with 2.5 µL sample loading volume. The ten different peptides with ten different peaks were separated by CITP/CZE using the sheathless interface of the present invention in full scan MS mode. Good separation was still observed when the initial sample loading volume reached 33% of the total volume of the separation capillary. Stable nanoESI at flow rate of 65 mL/min was maintained throughout the CITP/CZE-MS analysis.

Figure 4:
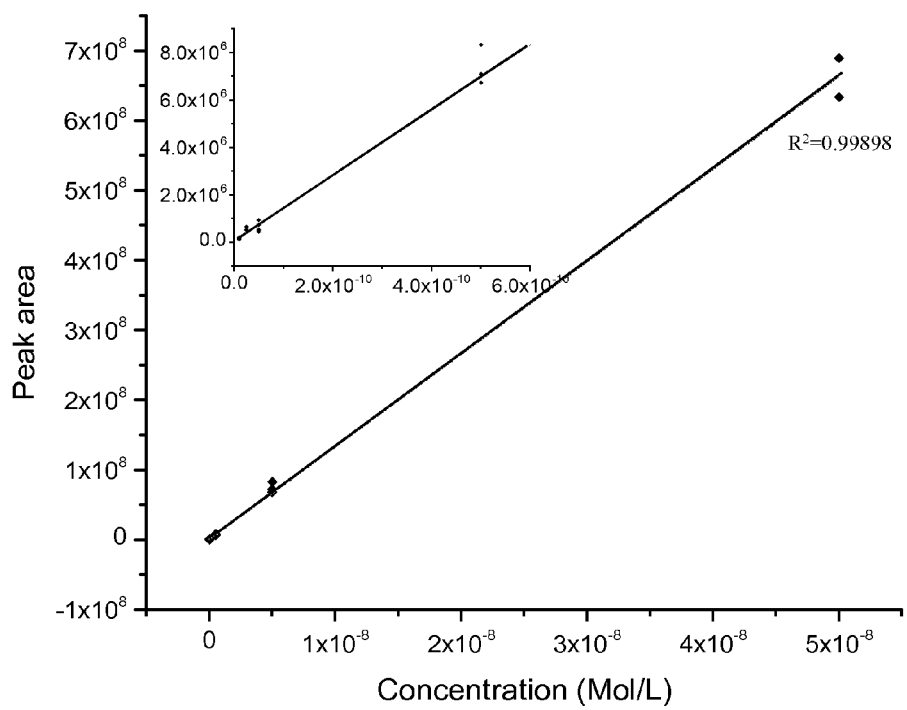
FIG. 4 shows the CITP/CZE-ESI-SRM MS quantitation of Kemptide, a targeted peptide, spiked in 50 nM bovine serum albumin (BSA) digest matrix at different concentrations.
Figure 5:
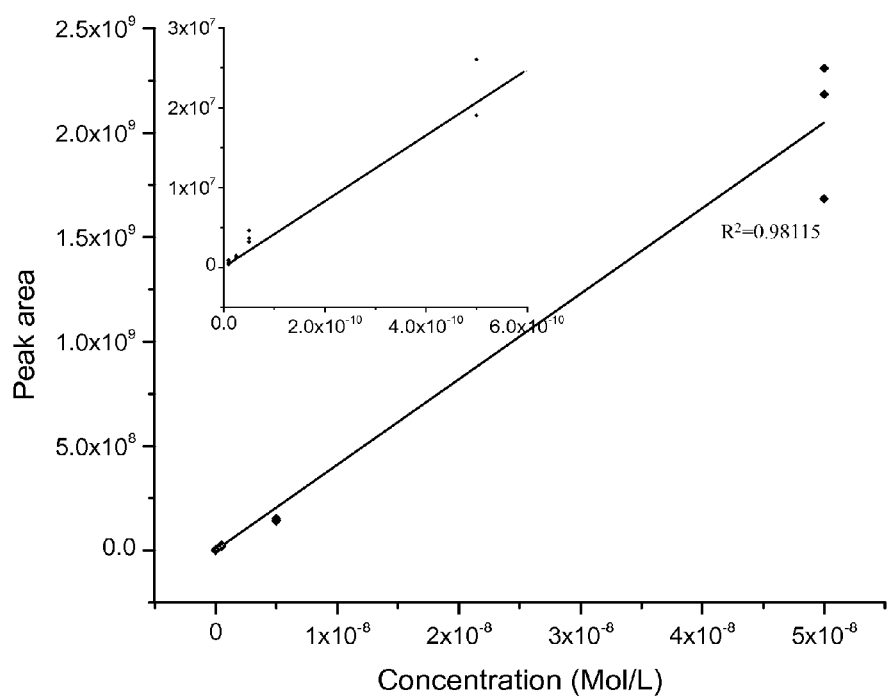
FIG. 5 shows the CITP/CZE-ESI-SRM MS quantitation of Angiotensin II, a targeted peptide, spiked in 50 nM BSA digest matrix at different concentrations.

The benefit of using the sheathless interface of the present invention to achieve both high sample loading capacity and ESI or nanoESI operation to significantly improve the sensitivity of CITP/CZE-MS was further evaluated for quantitative measurements of targeted peptides in the complex matrix. In this example, the triple quadrupole was operated in a special selected ion monitoring (SRM) mode in which a specific precursor to fragment ion transition was monitored for each selected peptide, as illustrated in FIG. 2. FIGS. 4 and 5 show the CITP/CZE-ESI-SRM MS quantitation of two targeted peptides, Kemptide (FIG. 4) and Angiotensin II (FIG. 5), spiked in 50 nM bovine serum albumin (BSA) digest matrix at different concentrations. Linearity was observed for both peptides in the tested concentration range, and a 10 pM limit of quantitation was demonstrated for both targeted peptides.

The coupling of CE with MS using the sheathless interface of the present invention enables high-volume sample loading and ultrasensitive and fast analysis in many fields of application. This appears to overcome a major barrier to more widespread use of the CE-MS technique.

The present invention has been described in terms of specific embodiments incorporating details to facilitate the understanding of the principles of construction and operation of the invention. As such, references herein to specific embodiments and details thereof are not intended to limit the scope of the claims appended hereto. It will be apparent to those skilled in the art that modifications can be made in the embodiments chosen for illustration without departing from the spirit and scope of the invention.

We claim:

1. A sheathless interface for coupling capillary electrophoresis (CE) with mass spectrometry comprising:
   a. a separation capillary for performing CE separation;
   b. an emitter capillary for electrospray ionization; wherein a portion of the emitter capillary is porous or is coated to form an electrically conductive surface, and wherein a section of the emitter capillary is disposed within the separation capillary, forming a joint; and
   c. a metal tube containing a conductive liquid and enclosing the joint, wherein the emitter capillary and the separation capillary have different diameters.

2. The sheathless interface of claim 1 wherein an outer diameter of the emitter capillary is smaller than an inner diameter of the separation capillary.

3. The sheathless interface of claim 1 wherein the inner diameter of the separation capillary is at least 75 μm and the outer diameter of the emitter capillary is less than 75 μm.

4. The sheathless interface of claim 1 wherein an emitter voltage is applied to the metal tube containing the conductive liquid and a separation voltage is applied to a non-sealed end of the separation capillary.

5. The sheathless interface of claim 4 wherein the emitter capillary is sealed at the joint of the separation and emitter capillaries.

6. The sheathless interface of claim 5 wherein the non-sealed end of the emitter capillary is coupled to a mass spectrometer instrument.

7. The sheathless interface of claim 6 wherein the mass spectrometer instrument is at least one of the following: a quadrupole mass spectrometer, a time of flight mass spectrometer, an ion trap mass spectrometer, Fourier transform ion cyclotron resonance mass spectrometer, and Orbitrap mass spectrometer.

8. The sheathless interface of claim 4 wherein a liquid is pumped to the non-sealed end of the separation capillary.

9. The sheathless interface of claim 1 wherein the CE separation includes at least one of the following: capillary zone electrophoresis (CZE) separation, capillary isotachophoresis (CITP), capillary Isoelectric Focusing (CIEF), and capillary electrochromatography.

10. The sheathless interface of claim 1 wherein the electrically conductive surface is a metallized surface.

11. A method of providing a sheathless interface for coupling capillary electrophoresis with mass spectrometry comprising:
   a. disposing a section of an emitter capillary within a separation capillary, thereby forming a joint;
   b. chemically etching a portion of the emitter capillary to form a porous capillary wall; and
   c. enclosing the joint in a metal tube that contains conductive liquid for electric contact, wherein the emitter capillary and the separation capillary have different diameters.

12. The method of claim 11 further comprising applying an emitter voltage to the metal tube containing the conductive liquid and a separation voltage to a non-sealed end of the separation capillary.

13. The method of claim 12 further comprising coupling the non-sealed end of the emitter capillary to a mass spectrometer instrument.

14. The method of claim 12 further comprising pumping liquid to the non-sealed end of the separation capillary.

15. The method of claim 11 further comprising sealing the emitter capillary at the joint of the separation and emitter capillaries.

16. The method of claim 11 wherein an outer diameter of the emitter capillary is smaller than an inner diameter of the separation capillary.

17. A method of providing a sheathless interface for coupling capillary electrophoresis with mass spectrometry comprising:
   a. disposing a section of an emitter capillary within a separation capillary, thereby forming a joint;
   b. coating a portion of the emitter capillary to form a metallized surface; and
   c. enclosing the joint in a metal tube that contains conductive liquid for electric contact, wherein the emitter capillary and the separation capillary have different diameters.

18. The method of claim 17 further comprising applying an emitter voltage to the metal tube containing the conductive liquid and a separation voltage to a non-sealed end of the separation capillary.

19. The method of claim 18 further comprising coupling the non-sealed end of the emitter capillary to a mass spectrometer instrument.

20. The method of claim 18 further comprising pumping liquid to the non-sealed end of the separation capillary.

21. The method of claim 17 further comprising sealing the emitter capillary at the joint of the separation and emitter capillaries.

22. The method of claim 17 wherein an outer diameter of the emitter capillary is smaller than an inner diameter of the separation capillary.

* * * * *